US008071570B2

(12) United States Patent
Viskov et al.

(10) Patent No.: US 8,071,570 B2
(45) Date of Patent: *Dec. 6, 2011

(54) MIXTURES OF POLYSACCHARIDES DERIVED FROM HEPARIN, THEIR PREPARATION AND PHARMACEUTICAL COMPOSITIONS CONTAINING THEM

(75) Inventors: Christian Viskov, Combs la Ville (FR); Vesna Biberovic, Aulnay-sous-Bois (FR); Pierre Mourier, Charenton la Pont (FR); Luc Grondard, Courcouronnes (FR)

(73) Assignee: Aventis Pharma S.A., Antony Cedex (FR)

(*) Notice: Subject to any disclaimer, the term of this patent is extended or adjusted under 35 U.S.C. 154(b) by 0 days.

This patent is subject to a terminal disclaimer.

(21) Appl. No.: 13/103,960

(22) Filed: May 9, 2011

(65) Prior Publication Data

US 2011/0201573 A1 Aug. 18, 2011

Related U.S. Application Data

(63) Continuation of application No. 11/882,607, filed on Aug. 2, 2007, now Pat. No. 8,003,623, which is a continuation of application No. 10/680,934, filed on Oct. 8, 2003, now abandoned.

(60) Provisional application No. 60/430,095, filed on Dec. 2, 2002.

(30) Foreign Application Priority Data

Oct. 10, 2002 (FR) .................................. 02 12584

(51) Int. Cl.
A61K 31/727 (2006.01)
C08B 37/10 (2006.01)
C07H 5/06 (2006.01)

(52) U.S. Cl. .............................. 514/56; 536/21; 536/55.1

(58) Field of Classification Search .................. None
See application file for complete search history.

(56) References Cited

U.S. PATENT DOCUMENTS

| 4,396,762 A | 8/1983 | Langer et al. |
| 4,401,662 A | 8/1983 | Lormeau et al. |
| 4,438,108 A | 3/1984 | Sanders et al. |
| 4,629,699 A | 12/1986 | Bianchini |
| 4,686,288 A | 8/1987 | Lormeau et al. |
| 4,692,435 A | 9/1987 | Lormeau et al. |
| 4,777,161 A | 10/1988 | Lormeau et al. |
| 4,801,583 A | 1/1989 | Petitou et al. |
| 4,847,338 A | 7/1989 | Linhardt et al. |
| 4,981,955 A | 1/1991 | Lopez et al. |
| 5,034,520 A | 7/1991 | Lormeau et al. |
| 5,039,529 A | 8/1991 | Bergendal et al. |
| 5,084,564 A | 1/1992 | Vila et al. |
| 5,272,261 A | 12/1993 | Cardin et al. |
| 5,389,618 A | 2/1995 | Debrie |
| 5,470,965 A | 11/1995 | Baldacci et al. |
| 5,690,910 A | 11/1997 | Ahmed et al. |
| 5,705,493 A | 1/1998 | Ferrari |
| 5,707,973 A | 1/1998 | Baron et al. |
| 5,849,703 A | 12/1998 | Wun |
| 5,849,721 A | 12/1998 | Uzan |
| 5,958,899 A | 9/1999 | Zoppetti et al. |
| 6,020,323 A | 2/2000 | Cohen et al. |
| 6,028,061 A | 2/2000 | Bernfield et al. |
| 6,197,943 B1 | 3/2001 | Casu et al. |
| 6,271,215 B1 | 8/2001 | Parish et al. |
| 6,288,044 B1 | 9/2001 | Zoppetti et al. |
| 6,384,021 B1 | 5/2002 | Mardiguian |
| 6,486,137 B1 | 11/2002 | Lundqvist et al. |
| 6,617,316 B1 | 9/2003 | Mourier et al. |
| 6,969,705 B2 | 11/2005 | Pecquet et al. |
| 2002/0009782 A1 | 1/2002 | Miron |
| 2002/0010153 A1 | 1/2002 | Byun et al. |
| 2002/0019368 A1 | 2/2002 | Mourier et al. |
| 2002/0062019 A1 | 5/2002 | Oreste et al. |
| 2002/0169143 A1 | 11/2002 | Sasisekharan et al. |
| 2003/0181416 A1 | 9/2003 | Comper |
| 2003/0203385 A1 | 10/2003 | Venkataraman et al. |
| 2004/0038932 A1 | 2/2004 | Hirsh et al. |
| 2005/0009782 A1 | 1/2005 | Comper et al. |
| 2005/0020536 A1 | 1/2005 | Branellec et al. |
| 2005/0119469 A1 | 6/2005 | Smith |
| 2008/0182820 A1* | 7/2008 | Viskov ........................ 514/56 |
| 2011/0178039 A1* | 7/2011 | Laux et al. .................. 514/56 |

FOREIGN PATENT DOCUMENTS

| CN | 101531723 A | 9/2009 |
| EP | 0 040 144 A1 | 5/1981 |
| EP | 0 133 078 A1 | 7/1984 |
| EP | 0 138 632 A2 | 7/1984 |
| EP | 0 293 539 A2 | 12/1988 |
| JP | 2001-240607 | 9/2001 |
| WO | WO 94/29352 | 12/1994 |
| WO | WO 01/02443 | 1/2001 |
| WO | WO 03/072611 | 9/2003 |
| WO | WO 2004/017910 | 3/2004 |

OTHER PUBLICATIONS

Choay et al., "Structural Studies on a Biologically Active Hexasaccharide Obtained from Heparin" Annals of the New York Academy of Sciences (1981) vol. 370 pp. 644-649.*

Choay et al., :Structural Studies on a biologically active hexasaccharide obtained from Heparin., Annals NY Acad Sco. 1981; 370:644-649.

* cited by examiner

*Primary Examiner* — Eric S Olson

(74) *Attorney, Agent, or Firm* — McCarter & English, LLP

(57) ABSTRACT

The present invention relates to mixtures of polysaccharides derived from heparin having a mean molecular weight of 1500 to 3000 Daltons and an anti-Xa/anti-IIa ratio greater than 30, their method of preparation and pharmaceutical compositions containing them.

7 Claims, No Drawings

MIXTURES OF POLYSACCHARIDES DERIVED FROM HEPARIN, THEIR PREPARATION AND PHARMACEUTICAL COMPOSITIONS CONTAINING THEM

CROSS-REFERENCE TO RELATED APPLICATIONS

This application is a continuation of U.S. Ser. No. 11/882,607, filed Aug. 2, 2007, which is a continuation of U.S. Ser. No. 10/680,934, filed Oct. 8, 2003, now abandoned, which, in turn, claims the benefit of priority from French Patent Application No. 0212584, filed Oct. 10, 2002, as well as the benefit of U.S. Provisional Application No. 60/430,095, filed Dec. 2, 2002. The contents of these applications are incorporated herein by reference in their entireties.

FIELD OF THE INVENTION

The present invention relates to mixtures of polysaccharides derived from heparin, their method of preparation and pharmaceutical compositions containing them.

BACKGROUND OF THE INVENTION

Heparin is a mixture of sulfated mucopolysaccharides of animal origin which is used in particular for its anticoagulant and antithrombotic properties.

Heparin nevertheless has disadvantages which limit the conditions for its use. In particular, its high anticoagulant activity (anti-IIa activity) can cause hemorrhages.

Low-molecular-weight heparins obtained by basic depolymerization of heparin esters have been proposed (EP40144); however, these products still have a high anti-IIa (aIIa) activity.

Very-low-molecular-weight heparins have also been described in U.S. Pat. No. 6,384,021. However, the anti-Xa (aXa) activity values obtained in the examples described do not exceed 120 IU, and the anti-Xa/anti-IIa ratio obtained is between 15 and 50.

In WO-0208295, very-low-molecular-weight heparins are prepared by a method different from that of U.S. Pat. No. 6,384,021 and exhibit an activity between 100 and 150 IU, with anti-Xa/anti-IIa ratios which are also very high for certain examples of application.

A constant need however exists in this class of medicament to improve the anti-Xa activities, in particular, in obtaining activities greater than 150 IU/mg, as well as the anti-Xa/anti-IIa ratio; and therefore to develop novel generations of heparin derivatives.

SUMMARY OF THE INVENTION

The invention, therefore, provides products having improved anti-Xa activity and anti-Xa/anti-IIa ratio by modifying the methods described in the prior art, in particular, by controlling the percentage of water during the depolymerization step. The modified heparins thus obtained exhibit an excellent antithrombotic activity and possess an aXa activity similar to very low aIIa activity. Likewise, the products of the invention exhibit half-life periods which are markedly greater than that of heparin.

The invention therefore provides novel mixtures of polysaccharides derived from heparin possessing a more selective activity toward activated factor X (factor Xa) and toward activated factor II (factor IIa) than heparin.

It is understood that the mixtures of polysaccharides having a mean molecular weight in the range of about 1500 to 3000 Da can be termed oligosaccharides.

DETAILED DESCRIPTION OF THE INVENTION

More particularly, the present invention provides mixtures of sulfated oligosaccharides having the general structure of the constituent polysaccharides of heparin and having the following characteristics:

they have a mean molecular weight of about 1500 to 3000 daltons, an anti-Xa activity of about 120 to 200 IU/mg, an anti-IIa activity of less than about 10 IU/mg and an anti-Xa activity/anti-IIa activity ratio of greater than about 30, the constituent oligosaccharides of the mixtures contain 2 to 26 saccharide units, have a 4,5-unsaturated uronic acid 2-O-sulfate unit at one of their ends, and contain the hexasaccharide ΔIIa-IIs-Is of formula:

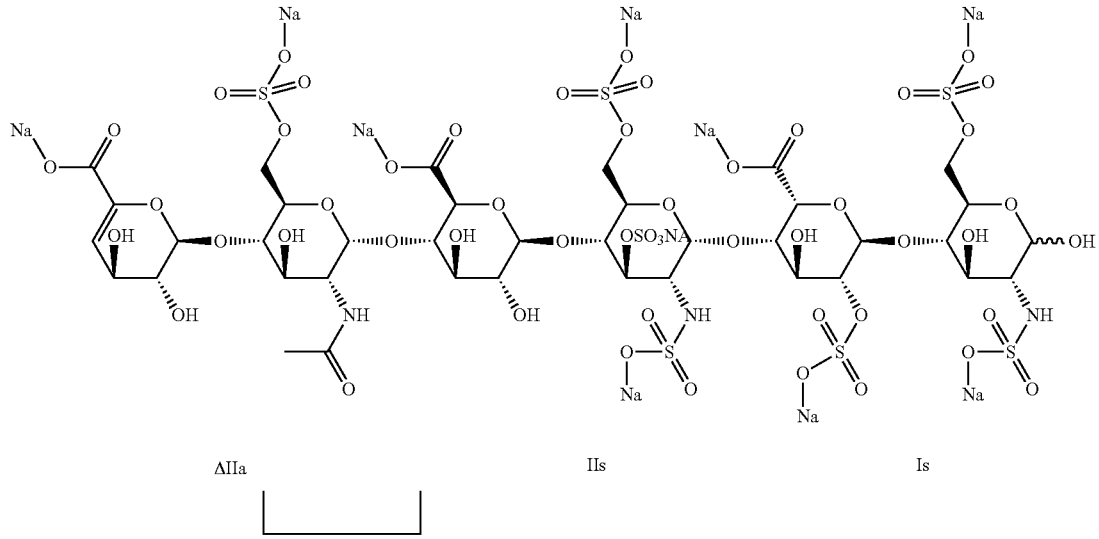

The hexasaccharide ΔIIa-IIs-Is contained in the mixture of oligosaccharides described in the present invention is a sequence which has a high affinity for ATIII and is characterized by an aXa activity greater than 740 U/mg.

The mixture of oligosaccharides described in the present invention is in the form of an alkali or alkaline-earth metal salt.

As the alkali or alkaline-earth metal salt, the sodium, potassium, calcium and magnesium salts are preferred.

The mean molecular weight is determined by high-pressure liquid chromatography using two columns in series, for example those marketed under the names TSK G3000 XL and TSK G2000 XL. The detection is carried out by refractometry. The eluent used is lithium nitrate and the flow rate is 0.6 ml/min. The system is calibrated with standards prepared by fractionation of enoxaparin (AVENTIS) by chromatography on agarose-polyacrylamide gel (IBF). This preparation is carried out according to the technique described by Barrowcliffe et al., Thromb. Res., 12, 27-36 (1977-78) or D. A. Lane et al., Thromb. Res., 12, 257-271 (1977-78). The results are calculated with the GPC6 software (Perkin Elmer).

The anti-Xa activity is measured by the amidolytic method on a chromogenic substrate described by Teien et al., Thromb. Res., 10, 399-410 (1977), with, as standard, the first international standard for low-molecular-weight heparins. See Barrowcliffe, T. W., A. D. Curtis, et al. (1985). "Standardization of Low Molecular Weight Heparins: A Collaborative Study." *Thrombosis and Haemostasis* 54: 675-679; and Barrowcliffe, T. W. (1988). "An International Standard for Low Molecular Weight Heparin." *Thrombosis and Haemostasis* 60:1-7.

The anti-IIa activity is measured by the technique described by Anderson L. O. et al., Thromb. Res., 15, 531-541 (1979), with, as standard, the first international standard for low-molecular-weight heparins.

The hexasaccharide fraction preferably represents from about 15 to 25% of the mixture of oligosaccharides.

Preferably, the mixtures according to the invention contain from about 8 to 15% of the hexasaccharide ΔIIa-IIs-Is in the hexasaccharide fraction of the mixture of oligosaccharides.

The percentage of the hexasaccharide fraction may be analytically determined by high-pressure liquid chromatography on TSK G3000 XL and TSK G2000 XL columns or, alternatively, by preparative separation of the hexasaccharide fraction. The mixture is, in this case, chromatographed on columns filled with a polyacrylamide agarose type gel, such as that marketed under the trademark Ultrogel ACA202$^R$ (Biosepra). The mixture is eluted with a sodium hydrogen carbonate solution. Preferably, the sodium hydrogen carbonate solution is a 0.1 mol/l to 1 mol/l solution. Still more preferably, the separation is carried out at a concentration of 1 mol/l. The determination is carried out by UV spectrometry (254 nm). After fractionation, the hexasaccharide fraction in solution in sodium hydrogen carbonate is neutralized with glacial acetic acid. The solution is then concentrated under reduced pressure so as to obtain a sodium acetate concentration greater than 30% by weight. The hexasaccharide fraction is precipitated by adding from 3 to 5 volumes of methanol. The hexasaccharide fraction is recovered by filtration on No. 3 sintered glass filtration funnel. The hexasaccharide mixture obtained may be analyzed by HPLC (High-Performance Liquid Chromatography) in order to determine the content of hexasaccharide ΔIIa-IIs-Is. Hexasaccharide ΔIIa-IIs-Is may be isolated by preparative HPLC chromatography or by affinity chromatography on an antithrombin III sepharose column according to the techniques used by persons skilled in the art (M. Hook, I. Bjork, J. Hopwood and U. Lindahl, *F.E.B.S letters*, vol 656(1) (1976)).

Most preferably, the mixtures according to the invention have an anti-Xa activity of between about 150 IU/mg and 200 IU/mg.

Preferably, the mixtures according to the invention have an anti-IIa activity of less than about 5 IU/mg, and, most preferably, of about 0.5 to 3.5 IU/mg. The examples of applications described below demonstrate values of between 1.1 and 1.6 IU/mg when the preferred characteristics of the process are used.

Preferably, the mixtures exhibit an anti-Xa activity/anti-IIa activity ratio greater than about 50 and most preferably greater than about 100.

Preferably, the mixtures according to the invention have a mean molecular weight of between about 2000 and 3000 Daltons, and most preferably a mean molecular weight of between 2400 and 2650 Da.

The present invention therefore preferably provides the mixtures as defined above, having an anti-Xa activity of between about 150 and 200 IU/mg, an anti-IIa activity of between about 0.5 and 3.5 IU/mg and a mean molecular weight of between about 2400 and 2650 Da.

The mixtures of oligosaccharides according to the invention may be prepared by depolymerization of a quaternary ammonium salt of the benzyl ester of heparin in an organic medium, by means of a strong organic base with a pKa preferably greater than 20 (properties preferably similar to the family of phosphazenes defined, for example, according to R. Schwesinger et al., Angew. Chem. Int. Ed. Engl. 26, 1167-1169 (1987), R. Schwesinger et al., Angew. Chem. 105, 1420 (1993)), conversion of the quaternary ammonium salt of the benzyl ester of the depolymerized heparin to a sodium salt, saponification of the residual esters and, optionally, purification. The method according to the invention repeats the main steps of the method described in WO 0208295 while adding an essential characteristic which makes it possible to obtain the mixtures of oligosaccharides according to the invention with the physicochemical characteristics and the activities described above.

Indeed, in order to obtain the specific mixtures of oligosaccharides according to the invention, it is necessary to control the selectivity of the base by a very precise control of the water content of the mixture during the depolymerization step.

The method according to the present invention is indeed characterized by a control of the high selectivity of the base during the depolymerization. It makes it possible to depolymerize the heparin while preserving as much as possible the sequences with an affinity for ATIII such as the hexasaccharide ΔIIa-IIs-Is described herein. This critical step of the method makes it possible to obtain the polysaccharides according to the invention.

This characteristic of the method results in unexpected aXa activities in terms of the mean molecular weight of the mixtures of oligosaccharides (150 IU/mg<aXa<200 IU/mg for a mean molecular weight of between 2000 Da and 3000 Da). This selectivity is due to the very particular physicochemical characteristics of the phosphazene bases which have a pKa greater than 20, a very high steric hindrance and a weak nucleophilicity.

This effect is fully expressed when the reaction medium is anhydrous. On the other hand, when the water content of the reaction medium increases, a drastic reduction in the selectivity of the depolymerization is observed. The preservation of the sequences with affinity for ATIII decreases, and the consequence is a large drop in the aXa activity. In the presence of a low quantity of water, the phosphazene base becomes protonated and the reactive species becomes a quaternary ammonium hydroxide. In this case, the very high steric hindrance and weak nucleophilicity properties are lost and greatly influence the quality of the product obtained. When depolymerization trials are carried out with a measured and controlled water content, this effect can be seen to be fully expressed.

The following table summarizes the impact of the water content on the selectivity of the depolymerization. (Only this parameter is variable in the trials: the stoichiometry of the reagents, the dilutions, and the temperatures remain constant according to the criteria of persons skilled in the art. The base used is the phosphazene base: 2-tert-butylimino-2-diethylamino-1,3-dimethylperhydro-1,2,3-diazaphosphorine.):

|  | Water content % | | | | | | | |
| --- | --- | --- | --- | --- | --- | --- | --- | --- |
|  | 0.05% | 0.1% | 0.2% | 0.3% | 0.4% | 0.57% | 1.8% | 2.5% |
| aXa IU/mg | 192 | 177 | 161 | 132 | 122 | 120 | 105 | 99 |
| aIIa IU/mg | 1.3 | 1.5 | 1.4 | 1.4 | 1.3 | 1.4 | 3.1 | 13.4 |
| aXa/ aIIa | 148 | 118 | 115 | 94 | 94 | 85.7 | 34 | 7.4 |

For an optimum selectivity and a maximum preservation of the sequences with affinity for ATIII, it is preferable to carry out the procedure at water contents of less than about 0.6% and, most preferably, less than about 0.3% when 1 molar equivalent of phosphazene base is used relative to the benzyl ester of heparin, benzethonium salt.

The method of the invention is therefore most particularly characterized by the step of depolymerization of the quaternary ammonium salt of the benzyl ester of heparin obtained according to methods known to persons skilled in the art, wherein a base of the family of phosphazenes, particularly in a dichloromethane solution containing a percentage of water of less than 0.6%, is used. Preferably, this percentage of water should be less than 0.3% and, most preferably, less than 0.2%.

Advantageously, the strong base/ester mol ratio is between 0.2 and 5, preferably between 0.6 and 2 and most preferably between 0.8 and 1.2. The use of the equimolar ratio therefore forms part of the preferred embodiments of the invention.

Other aprotic solvents known to persons skilled in the art may be used, such as THF or DMF.

The quaternary ammonium salt of the benzyl ester of heparin is preferably the benzethonium, cetylpyridinium or cetyltrimethylammonium salt.

The bases of the family of phosphazenes are preferably those of formula:

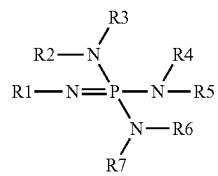

in which the radicals R1 to R7 are identical or different and represent alkyl radicals.

In the preceding formulae, the alkyl radicals contain 1 to 6 carbon atoms in the form of a straight or branched chain.

The invention therefore provides a method for preparing the mixtures of oligosaccharides of the invention, this method comprising the following steps:
a) transalification of sodium heparin by the action of benzethonium chloride,
b) esterification of benzethonium heparinate by the action of benzyl chloride,
c) transalification of the benzyl ester obtained to a quaternary ammonium salt,
d) depolymerization of the quaternary ammonium salt of the benzyl ester of heparin by the method as defined above,
e) conversion of the quaternary ammonium salt to a sodium salt,
f) optionally, saponification of the heparin by the action of a base such as sodium hydroxide,
g) optionally, purification in particular by the action of an oxidizing agent such as hydrogen peroxide.

The following reaction scheme illustrates the method of the present invention:

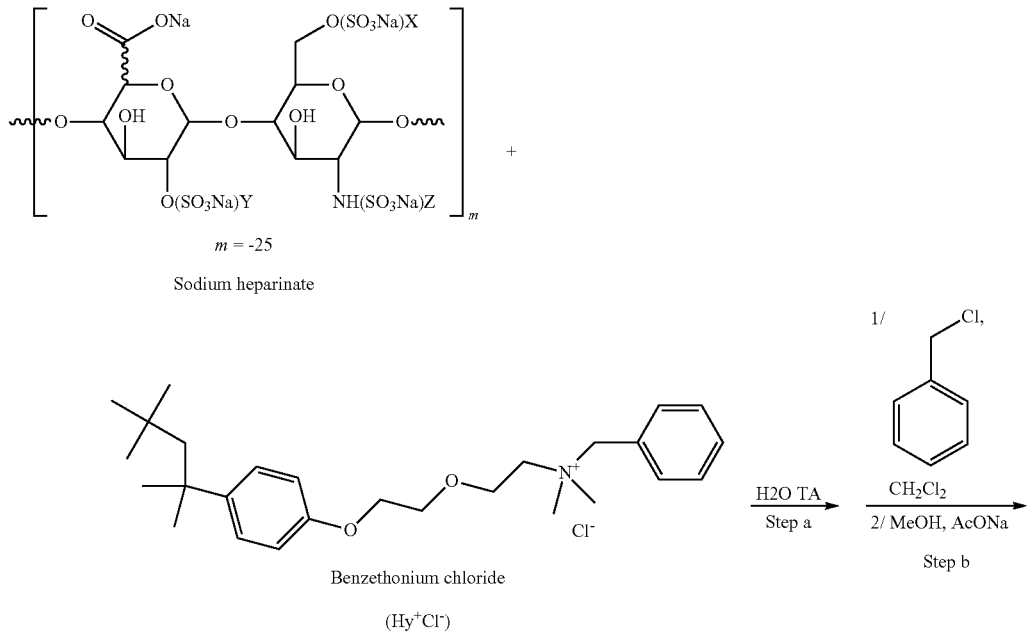

-continued

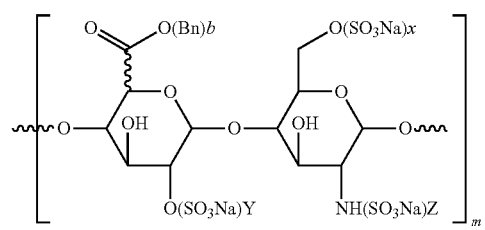

b = degree of esterification

Crude benzyl ester

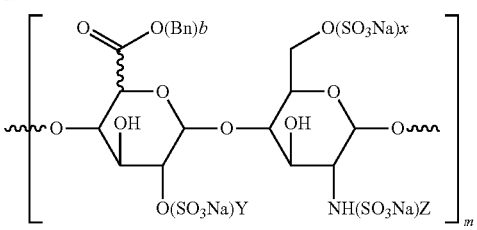

b = degree of esterification

Pure benzyl ester, sodium salt

Purification

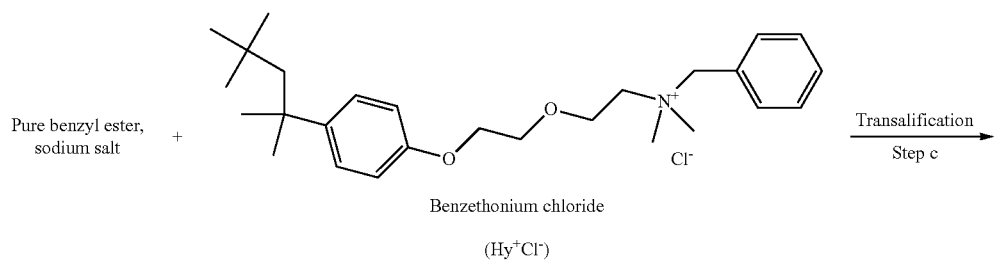

Pure benzyl ester, sodium salt  +  Benzethonium chloride (Hy⁺Cl⁻)

Transalification
Step c

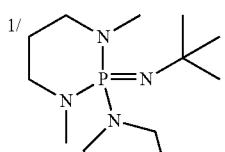

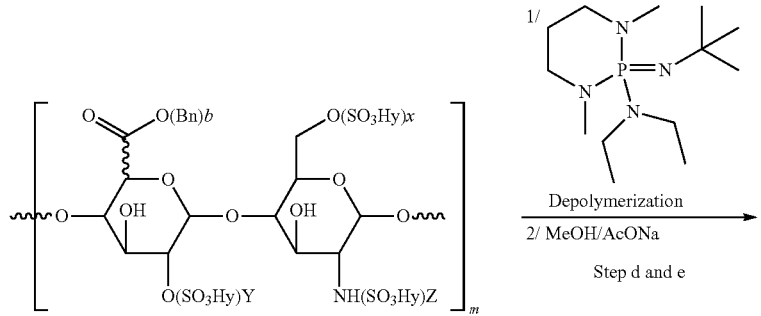

m = ~25

Pure benzyl ester, benzethonium salt

Depolymerization
1/ [phosphazene base]
2/ MeOH/AcONa
Step d and e

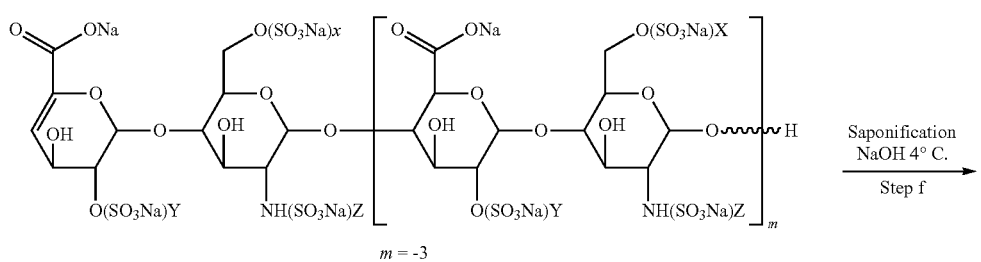

m = ~3

Crude ULMWH (residual esters)

Saponification
NaOH 4° C.
Step f

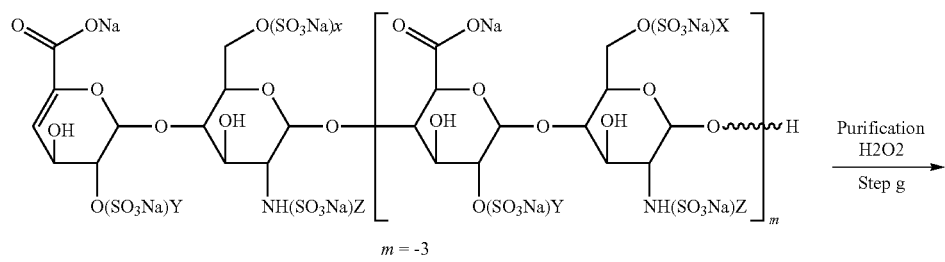

m = ~3

Crude ULMWH

Purification
H2O2
Step g

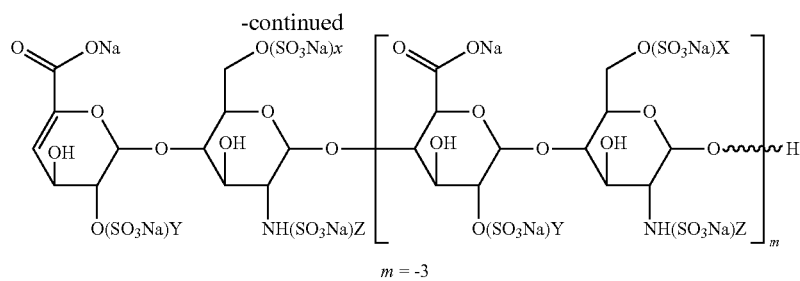

m = -3 pure ULMWH

N = X + Y + Z (mean overall level of sulfation of the disaccharide)
X = Degree of sulfation of the site, the remainder is represented by the radical H
Y = Degree of sulfation of the site, the remainder is represented by the radical H
Z = Degree of sulfation of the site, the remainder is represented by the radical COCH$_3$ The conversion of the quaternary ammonium salt of the benzyl ester of the depolymerized heparin to a sodium salt (step e) is generally carried out by treating the reaction medium with an alcoholic solution of sodium acetate and preferably with a 10% solution of sodium acetate in methanol (weight/volume), at a temperature of between 15 and 25° C. The equivalent by weight of acetate added is preferably 3 times greater than that of the quaternary ammonium salt of the benzyl ester of heparin used in the depolymerization reaction.

The saponification (step f) is generally carried out by means of an alkali metal hydroxide such as sodium hydroxide, potassium hydroxide or lithium hydroxide, in an aqueous medium, at a temperature of between 0 and 20° C. and preferably between 0 and 10° C. 1 to 5 molar equivalents of alkali metal hydroxide will be generally used. Preferably, the saponification will be carried out in the presence of 1 to 2 molar equivalents of alkali metal hydroxide.

The final product may be optionally purified (step g) by any known method of purifying depolymerized heparins (for example, that disclosed in EP 0037319B1). Preferably, the purification is carried out by means of hydrogen peroxide, in an aqueous medium, at a temperature of 10 to 50° C. Preferably, this operation is carried out at a temperature between 20 and 40° C.

The quaternary ammonium salt of the benzyl ester of heparin may be prepared according to the following steps:
a) conversion of the heparin to the form of a sodium salt by means of benzethonium chloride in order to obtain benzethonium heparinate (transalification),
b) esterification of the benzethonium salt obtained in step a) above by means of benzyl chloride and treatment with an alcoholic solution of sodium acetate in order to obtain the sodium salt of the benzyl ester of heparin,
c) transalification of the sodium salt of the benzyl ester of heparin to a quaternary ammonium salt and preferably to a benzethonium, cetylpyridinium or cetyltrimethylammonium salt.

The reaction of step a) is carried out by the action of benzethonium chloride in excess, on sodium heparin, at a temperature in the region of 15 to 25° C. Advantageously, the salt/sodium heparin molar ratio is between 3 and 4.

The starting heparin used is preferably a pig heparin. The latter may be purified beforehand in order to reduce its dermatan sulfate level according to the method described in patent FR2663639.

The esterification of step b) is preferably carried out in a chlorinated organic solvent (for example chloroform or methylene chloride (dichloromethane)), at a temperature of between 25 and 45° C. and preferably between 30 and 40° C. The ester in the form of a benzethonium salt is then recovered in the form of a sodium salt by precipitation by means of sodium acetate at 10% by weight in an alcohol such as methanol. 1 to 1.2 volumes of alcohol are generally used per volume of reaction medium. The quantity of benzyl chloride and the reaction time are adjusted in order to obtain a degree of esterification of between 50 and 100% and preferably between 70 and 90%. Preferably, 0.5 to 1.5 parts by weight of benzyl chloride are used for 1 part by weight of benzethonium salt of heparin. Likewise, preferably the reaction time will be between 10 and 35 hours.

The transalification step c) is carried out by means of a quaternary ammonium chloride and preferably by means of benzethonium chloride, cetylpyridinium chloride or cetyltrimethylammonium chloride, in an aqueous medium, at a temperature of between 10 and 25° C. Advantageously, the quaternary ammonium chloride/sodium salt of the benzyl ester of heparin mol ratio is between 2 and 3.

The mixtures according to the invention, in the form of a sodium salt, may be converted to another alkali or alkaline-earth metal salt. The passage from one salt to another is optionally achieved using the method described in patent FR 73 13 580.

The mixtures of oligosaccharides of the present invention are not toxic and may thus be used as medicaments.

The mixtures of oligosaccharides of the present invention may be used as antithrombotic agents. In particular, they are useful for the treatment or prevention of venous and arterial thromboses, deep vein thrombosis, pulmonary embolism, unstable angina, myocardial infarction, cardiac ischemia, occlusive diseases of the peripheral arteries and atrial fibrillation. They are also useful in the prevention and treatment of the proliferation of smooth muscle cells, atheriosclerosis and arteriosclerosis, for the treatment and prevention of cancer by modulating angiogenesis and growth factors, and for the treatment and prevention of diabetic disorders such as diabetic retinopathies and nephropathies.

The present invention also relates to pharmaceutical compositions containing, as an active ingredient, a mixture of formula (I), optionally in combination with one or more inert excipients.

The pharmaceutical compositions are, for example, solutions which can be injected by the subcutaneous or intravenous route. They are also useful for administration by the pulmonary route (inhalation) or by the oral route.

The dosage may vary according to the age, weight and state of health of the patient. For an adult, it is, in general, between about 20 and 100 mg per day by the intramuscular or subcutaneous route.

The following examples illustrate the invention without, however, limiting its scope.

Example A

Preparation of the Benzethonium Salt of Benzyl of Heparinate

Benzethonium Heparinate

A solution of 25 g of benzethonium chloride in 125 ml of water is added to a solution of 10 g of heparin in the form of a sodium salt in 100 ml of water. The product is filtered, washed with water and dried.

Benzyl Ester of Heparin (Sodium Salt)

16 ml of benzyl chloride are added to a solution of 20 g of benzethonium heparinate in 80 ml of methylene chloride. The solution is heated at a temperature of 30° C. for 12 hours. 108 ml of a 10% solution of sodium acetate in methanol are then added, the mixture is filtered, washed with methanol and dried. 7.6 g of benzyl ester of heparin are thus obtained in the form of a sodium salt whose degree of esterification is 77%.

Benzyl Ester of Heparin (Benzethonium Salt)

36 g (0.0549 mol) of benzyl ester of heparin (sodium salt) and 540 ml of distilled water are introduced into a 2-litre Erlenmeyer flask A. After homogenization at a temperature of about 20° C., a pale yellow solution is obtained. A solution of 64.45 g (0.1438 mol) of benzethonium chloride and 450 ml of water is prepared, with magnetic stirring, in a 1-litre Erlenmeyer flask B. The solution in Erlenmeyer B is poured over about 35 minutes into the solution in Erlenmeyer A, with stirring. The formation of an abundant white precipitate is observed. The Erlenmeyer B is rinsed with 200 ml of distilled water, and the wash water is introduced into the Erlenmeyer A. The stirring is then stopped and the suspension is allowed to settle for 12 hours. Once this time has elapsed, the clear portion of the supernatant is removed and discarded. 560 ml of water are added to the sedimented precipitate (slurry appearance) and the mixture is stirred for 20 minutes. The precipitate is allowed to resediment for about 30 minutes. The supernatant is removed and discarded (560 ml). This operation of washing with about 560 ml of distilled water is repeated twice on the sedimented precipitate. In the last washing operation, the precipitate is left in suspension and filtered through a No. 3 sintered glass filtration funnel. The cake is then washed with 4 times 200 ml of distilled water. The wet white solid is drained and then dried under reduced pressure (2.7 kPa) at a temperature of about 60° C. After drying for 12 hours, 87.5 g of benzyl heparinate, benzethonium salt, are obtained. The yield obtained is 94.9%.

Example B

Description of the Hexasaccharide ATIII (ΔIIa-IIs-Is)

Proton spectrum in $D_2O$, 500 MHz, T=298 K, δ in ppm: 1.97 (3H, s), 3.18 (1H, dd, 10 and 3 Hz), 3.30 (1H, t, 8 Hz), 3.37 (1H, dd, 10 and 3 Hz), 3.60 (2H, m), between 3.65 and 3.85 (6H, m), 3.87 (2H, m), 3.95 (1H, d, 8 Hz), 4.03 (1H, d, 8 Hz), between 4.05 and 4.13 (4H, m), between 4.16 and 4.45 (8H, m), 4.52 (1H, d, 8 Hz), 4.67 (1H, m), 5.06 (1H, d, 6 Hz), 5.10 (1H, d, 3 Hz), 5.33 (1H, d, 4 Hz), 5.36 (1H, d, 3 Hz), 5.46 (1H, d, 3 Hz), 5.72 (1H, d, 4 Hz).

Decasodium salt of 4-deoxy-α-L-threo-hexenepyranosyluronic acid-(1→4)-2-deoxy-2-acetamido-6-O-sulfo-α-D-glucopyranosyl-(1→4)-β-D-glucopyranosyluronic acid-(1→4)-2-deoxy-2-sulfamido-3,6-di-O-sulfo-α-D-glucopyranosyl)-(1→4)-2-O-sulfo-α-L-idopyranosyluronic acid-(1→4)-2-deoxy-2-sulfamido-6-O-sulfo-α-D-glucopyranose.

Examples 1 to 7 and 12 illustrate the influence of the water content on the selectivity of the polymerization reaction and the aXa and aIIa activity of the products obtained.

Examples 8 to 10 illustrate the influence of the number of base equivalents on the aXa and aIIa activity of the product obtained (with a water content of 0.1%).

Example 11 illustrates the use of a phosphazene base other than 2-tert-butylimino-2-diethylamino-1,3-dimethylperhydro-1,2,3-diazaphosphorine; that is, the use of tert-butyliminotri(pyrrolidino)phosphorane.

Example 1

Depolymerization and Conversion to the Sodium Salt (0.1% Water)

70 ml of dichloromethane are placed in an Erlenmeyer flask A. 10 g (0.006 mol) of benzyl ester of heparin (degree of esterification: 75%, benzethonium salt) obtained as described in example A are added slowly with stirring. The water content of the reaction medium is adjusted to 0.1%. The solution is heated to 40° C. under nitrogen. After total dissolution, the solution is cooled to a temperature of about 20° C., followed by addition of 1.75 ml (0.006 mol) of 2-tert-butylimino-2-diethylamino-1,3-dimethylperhydro-1,2,3-diazaphosphorine. The resulting mixture is stirred at a temperature of about 20° C. for 24 hours. During this time, a solution of 30 g of anhydrous sodium acetate in 300 ml of methanol is prepared in an Erlenmeyer flask B. After total dissolution, 5 g of Hyflo supercel Celite are added to the solution. The reaction mixture in the Erlenmeyer flask A is poured over 1 minute 30 seconds into the methanolic solution of sodium acetate at a

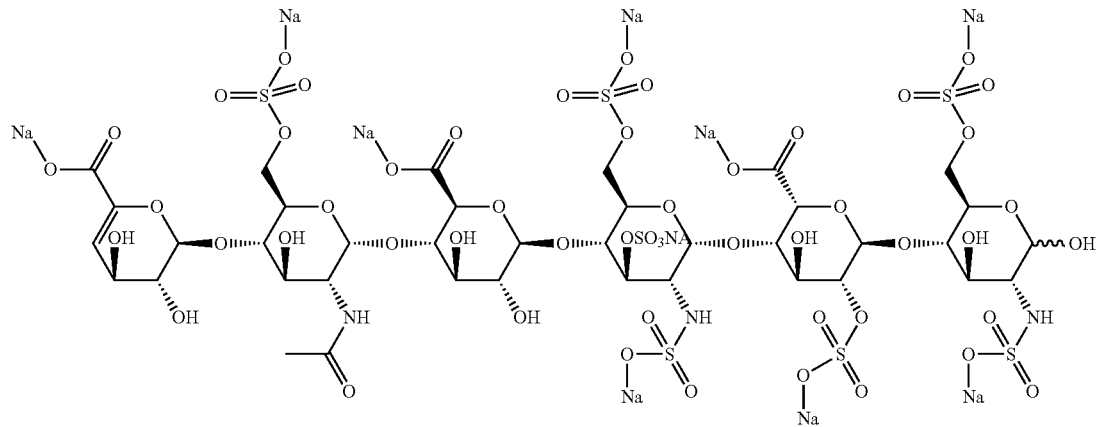

temperature of about 5° C., with magnetic stirring. After stirring for 5 minutes, the suspension is left to settle for 1 hour 30 minutes. The clear part of the supernatant is separated out and discarded (220 ml). 220 ml of methanol are added to the sedimented precipitate, and the mixture is stirred for 5 minutes. The precipitate is left to resediment for about 1 hour 20 minutes. The supernatant is separated out and discarded (250 ml). 250 ml of methanol are added to the sedimented precipitate, and the mixture is stirred for 5 minutes. The precipitate in suspension is then filtered through a No. 3 sintered glass filtration funnel. The cake obtained is then washed with 100 ml of methanol. The pale yellow wet solid is drained and then dried under reduced pressure (6 kPa) at a temperature of about 40° C. After drying for 18 hours, 2.51 g of the sodium salt of depolymerized heparin in Celite (5 g) are obtained. The yield obtained is 64%.

Saponification:

2.5 g (0.0038 mol) of the crude depolymerized heparin, sodium salt in Celite (5 g) obtained above, and 17 ml of water are placed in a 50 ml Erlenmeyer flask. The suspension is filtered through a No. 3 sintered glass filtration funnel and rinsed twice with 5 ml of water. The filtrate obtained is placed in a 150 ml Erlenmeyer flask. 0.4 ml (0.004 mol) of 30% caustic soda is introduced with magnetic stirring, at a temperature of about 5° C. After the addition, the mixture is stirred for 2 hours. The solution is neutralized by adding 1N HCl; then 3 g of sodium chloride are added. After dissolution, 21 ml of methanol are added to the reaction medium. After stirring for 15 minutes, 44 ml of methanol are added, followed by stirring for 1 hour. Stirring is then stopped, and the suspension is left to sediment for 45 minutes at a temperature of about 5° C. The supernatant is then separated out and discarded (90 ml). 90 ml of methanol are added to the sedimented precipitate and the mixture is stirred for 5 minutes. The precipitate is left to resediment for about 20 minutes. The supernatant is separated out and discarded (80 ml). 80 ml of methanol are added to the sedimented precipitate, and the mixture is stirred for 5 minutes. The precipitate in suspension is then filtered through a No. 3 sintered glass filtration funnel. The cake obtained is then washed with 50 ml of methanol. The wet solid is drained and then dried under reduced pressure (6 kPa) at a temperature of about 40° C. After drying for 18 hours, 1.31 g of crude depolymerized heparin (sodium salt) are obtained. The yield obtained is 66%.

Purification:

1.3 g of crude depolymerized heparin obtained above and 13 ml of distilled water are placed in a 50 ml Erlenmeyer flask. The mixture is brought to 40° C. with magnetic stirring. The pH is brought to 9.7±0.1 by addition of 1N sodium hydroxide. The reaction medium is filtered through a 0.45 µm membrane, and 0.07 ml of aqueous 30% hydrogen peroxide solution is added. After stirring for about 2 hours at a temperature of about 20° C., the mixture is neutralized by adding 1N HCl, followed by addition of 2 g of sodium chloride. The solution is then filtered through a 0.45 µm membrane, and 14 ml of methanol are then poured in. The solution is then cooled to 10° C. and stirred for about 15 minutes. 36 ml of methanol are then added, followed by stirring for 1 hour. Stirring is then stopped and the suspension is left to sediment for about 15 minutes. The supernatant is then separated out and discarded (50 ml). 50 ml of methanol are added to the sedimented precipitate and the mixture is stirred for 5 minutes. The precipitate is left to resediment for about 25 minutes. The supernatant is separated out and discarded (50 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 40° C. After drying for 18 hours, 1.13 g of pure depolymerized heparin (sodium salt) are obtained. The yield obtained is 87%. The characteristics of the depolymerized heparin thus obtained are as follows:

mean molecular weight: 2600 Daltons
anti-Xa activity: 177 IU/mg
anti-IIa activity: 1.5 IU/mg
anti-Xa activity/anti-IIa activity ratio: 118.

Example 2

Depolymerization and Conversion to the Sodium Salt (0.2%)

70 ml of dichloromethane are placed in an Erlenmeyer flask A. 10 g (0.006 mol) of the benzyl ester of heparin (degree of esterification: 75%, benzethonium salt) obtained as described in example A are added slowly, with stirring and under nitrogen pressure. The water content of the reaction medium is adjusted to 0.2%. After total dissolution, 1.75 ml (0.006 mol) of 2-tert-butylimino-2-diethylamino-1,3-dimethylperhydro-1,2,3-diazaphosphorine are added. The mixture is stirred for 24 hours at a temperature of about 20° C. During this time, a solution of 30 g of anhydrous sodium acetate in 300 ml of methanol is prepared in an Erlenmeyer flask B. After total dissolution, 5 g of Hyflo supercel Celite are added to the solution. The reaction mixture in the Erlenmeyer flask A is poured over 1 minute 30 seconds into the methanolic solution of sodium acetate with magnetic stirring, at a temperature of about 5° C. After stirring for 5 minutes, the suspension is left to settle for 2 hours. The clear part of the supernatant is separated out and discarded (220 ml). 220 ml of methanol are added to the sedimented precipitate and the mixture is stirred for 5 minutes. The precipitate is left to resediment for about 2 hours. The supernatant is separated out and discarded (230 ml). 230 ml of methanol are added to the sedimented precipitate. The precipitate in suspension is then filtered through a No. 3 sintered glass filter. The cake obtained is then washed with 150 ml of methanol. The pale yellow wet solid is drained and then dried under reduced pressure (6 kPa) at a temperature of about 40° C. After drying for 18 hours, 2.63 g of crude depolymerized heparin in Celite (5 g) are obtained. The yield obtained is 67%.

Saponification:

2.5 g (0.0038 mol) of the sodium salt of depolymerized heparin in Celite (5 g) obtained above and 18 ml of water are placed in a 50 ml Erlenmeyer flask. The suspension is filtered through a No. 3 sintered glass filtration funnel and rinsed twice with 5 ml of water. The filtrate obtained is placed in a 150 ml Erlenmeyer flask. 0.4 ml (0.004 mol) of 30% caustic soda is added with magnetic stirring, at a temperature of about 5° C. After the addition, the mixture is stirred for 2 hours. The solution is neutralized by adding 1N HCl; then 2 g of sodium chloride are added. 14 ml of methanol are poured into the reaction mixture. After stirring for 15 minutes, 36 ml of methanol are added, followed by stirring for 1 hour. Stirring is then stopped and the suspension is left to sediment for 45 minutes at a temperature of about 5° C. The supernatant is then separated out and discarded (80 ml). 80 ml of methanol are added to the sedimented precipitate and the mixture is stirred for 5 minutes. The precipitate in suspension is then filtered through a No. 3 sintered glass filtration funnel. The cake obtained is then washed with 50 ml of methanol. The wet solid is drained and then dried under reduced pressure (6 kPa)

at a temperature of about 40° C. After drying for 48 hours, 2.3 g of crude depolymerized heparin (sodium salt) are obtained. The yield obtained is 65%.
Purification:
1.4 g of crude depolymerized heparin obtained above and 15 ml of distilled water are placed in a 50 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.07 ml of aqueous 30% hydrogen peroxide solution is added. After stirring for about 2 hours at a temperature of about 40° C., the mixture is cooled to a temperature of about 20° C. and then neutralized by addition of 1N HCl. 2 g of sodium chloride are added to the reaction medium. The solution is then filtered through a 0.45 μm membrane, and 14 ml of methanol are then poured in. The solution is then cooled to 10° C. and stirred for 15 minutes. 36 ml of methanol are then added, followed by stirring for 1 hour. Stirring is then stopped and the suspension is left to sediment for 15 minutes. The supernatant is then separated out and discarded (40 ml). 40 ml of methanol are added to the sedimented precipitate (slurry appearance) and the mixture is stirred for 5 minutes. The precipitate is left to resediment for about 20 minutes. The supernatant is separated out and discarded (50 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 40° C. After drying for 18 hours, 1.2 g of pure depolymerized heparin (sodium salt) are obtained. The yield obtained is 86%.

The characteristics of the depolymerized heparin thus obtained are as follows:
mean molecular weight: 2650 daltons
anti-Xa activity: 161 IU/mg
anti-IIa activity: 1.4 IU/mg
anti-Xa activity/anti-IIa activity ratio: 115.

Example 3

Depolymerization and Conversion to the Sodium Salt (0.3% Water)

70 ml of dichloromethane are placed in an Erlenmeyer flask A. 10 g (0.006 mol) of benzyl ester of heparin (degree of esterification: 75%, benzethonium salt) obtained as described in example A are added with stirring and under nitrogen pressure. The water content of the reaction medium is adjusted to 0.3%. After total dissolution, 1.75 ml (0.006 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 30 g of anhydrous sodium acetate in 300 ml of methanol is prepared in a separate Erlenmeyer flask B. After total dissolution, 5 g of Hyflo supercel Celite are added to the solution. The reaction mixture in the Erlenmeyer flask A is poured over 1 minute 30 seconds into the methanolic sodium acetate solution (flask B) at a temperature in the region of 5° C., with magnetic stirring. After stirring for 5 minutes, the suspension is left to settle for 1 hour 10 minutes. The clear part of the supernatant is separated out and discarded (220 ml). 220 ml of methanol are added to the sedimented precipitate and the mixture is stirred for 5 minutes. The precipitate in suspension is then filtered through a No. 3 sintered glass filtration funnel. The cake obtained is then washed with 100 ml of methanol. The wet solid is drained and then dried under reduced pressure (6 kPa) at a temperature of about 40° C. After drying for 18 hours, 2.57 g of crude depolymerized heparin are obtained, as the sodium salt in Celite (5 g). The yield obtained is 66%.
Saponification:
2.5 g (0.0038 mol) of the sodium salt of crude depolymerized heparin in Celite (5 g) obtained above and 18 ml of water are placed in a 50 ml Erlenmeyer flask. The suspension is filtered through a No. 3 sintered glass filtration funnel, and rinsed twice with 5 ml of water. The filtrate obtained is placed in a 150 ml Erlenmeyer flask. 0.4 ml (0.004 mol) of 30% caustic soda is added with magnetic stirring, at a temperature of about 5° C. After the addition, the mixture is stirred for 2 hours.

The solution is neutralized by adding 1N HCl; then 3 g of sodium chloride are added. 15 ml of methanol are poured into the reaction mixture. After stirring for 15 minutes, 36 ml of methanol are added, followed by stirring for 1 hour. Stirring is then stopped, and the suspension is left to sediment for 1 hour. The supernatant is then separated out and discarded (70 ml). 70 ml of methanol are added to the sedimented precipitate, and the mixture is stirred for 5 minutes. The precipitate in suspension is then filtered through a No. 3 sintered glass filtration funnel. The cake obtained is then washed with 50 ml of methanol. The wet solid is drained and then dried under reduced pressure (6 kPa) at a temperature of about 40° C. After drying for 48 hours, 1.42 g of crude depolymerized heparin (sodium salt) are obtained. The yield obtained is 62%.
Purification:
1.4 g of crude depolymerized heparin obtained above and 14 ml of distilled water are placed in a 50 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.07 ml of aqueous 30% hydrogen peroxide solution is added. After stirring for about 2 hours at a temperature of about 20° C., the mixture is neutralized by adding 1N HCl, followed by addition of 2 g of sodium chloride. After dissolution, the solution is then filtered through a 0.45 μm membrane, and 14 ml of methanol are then poured in. The filtrate is then cooled to 10° C. and stirred for 15 minutes. 36 ml of methanol are then added, followed by stirring for about 1 hour. Stirring is then stopped and the suspension is left to sediment for 40 minutes. The supernatant is then separated out and discarded (50 ml). 50 ml of methanol are added to the sedimented precipitate (slurry appearance) and the mixture is stirred for 5 minutes.

The precipitate is left to resediment for about 25 minutes. The precipitate in suspension is then filtered through a No. 3 sintered glass filtration funnel. The white cake obtained is then washed with 50 ml of methanol. The wet solid is drained and then dried under reduced pressure (6 kPa) at a temperature in the region of 40° C. After drying for 18 hours, 1.24 g of pure depolymerized heparin (sodium salt) are obtained. The yield obtained is 89%.

The characteristics of the depolymerized heparin thus obtained are as follows:
mean molecular weight: 2400 daltons
anti-Xa activity: 132 IU/mg
anti-IIa activity: 1.4 IU/mg
anti-Xa activity/anti-IIa activity ratio: 94.

Example 4

Depolymerization and Conversion to the Sodium Salt (0.4% Water)

70 ml of dichloromethane are placed in a Erlenmeyer flask A. 10 g (0.006 mol) of benzyl ester of heparin (degree of esterification: 75%, benzethonium salt) obtained as described in example A, are added slowly, with stirring. The water content of the reaction medium is adjusted to 0.4%. The solution is heated to 30° C. under nitrogen. After total dissolution, the mixture is cooled to a temperature of about 20° C., followed by addition of 1.75 ml (0.006 mol) of 2-tert-butyl-imino-2-diethylamino-1,3-dimethylperhydro-1,2,3-diazaphosphorine. The mixture is stirred at a temperature of about 20° C. for 24 hours. During this time, a solution of 30 g of anhydrous sodium acetate in 300 ml of methanol is prepared in a separate Erlenmeyer flask B. After total dissolution, 5 g of Hyflo supercel Celite are added to the solution. The reaction mixture in the Erlenmeyer flask A is poured over 1 minute 30 seconds into the methanolic sodium acetate solution at a temperature of about 5° C., with magnetic stirring. After stirring for 5 minutes, the suspension is left to settle for 2 hours. The clear part of the supernatant is separated out and discarded (80 ml). 80 ml of methanol are added to the sedimented precipitate, and the mixture is stirred for 5 minutes. The precipitate is left to resediment for about 1 hour. The supernatant is separated out and discarded (80 ml). 80 ml of methanol are added to the sedimented precipitate, and the mixture is stirred for 5 minutes. The precipitate in suspension is then filtered through a No. 3 sintered glass filtration funnel. The cake obtained is then washed with 150 ml of methanol. The pale yellow wet solid is drained and then dried under reduced pressure (6 kPa) at a temperature of about 40° C. After drying for 18 hours, 3.25 g of crude depolymerized heparin are obtained, as the sodium salt in Celite (5 g). The yield obtained is 83%.

Saponification:

3.1 g (0.0018 mol) of the sodium salt of crude depolymerized heparin in Celite (10 g) obtained above and 21 ml of water are placed in a 50 ml Erlenmeyer flask. The suspension is filtered through a No. 3 sintered glass filtration funnel and rinsed twice with 6 ml of water. The filtrate obtained is placed in a 150 ml Erlenmeyer flask. 0.7 ml (0.007 mol) of 30% caustic soda is added with magnetic stirring, at a temperature of about 5° C. After the addition, the mixture is stirred for 2 hours. The solution is neutralized by adding 1N HCl; then 4 g of sodium chloride are added. 28 ml of methanol are poured into the reaction mixture. After stirring for 15 minutes, 72 ml of methanol are added, followed by stirring for 1 hour. Stirring is then stopped and the suspension is left to sediment for 1 hour. The supernatant is then separated out and discarded (90 ml). 90 ml of methanol are added to the sedimented precipitate, and the mixture is stirred for 5 minutes. The precipitate is left to resediment for about 20 minutes. The supernatant is separated out and discarded (90 ml). 90 ml of methanol are added to the sedimented precipitate, and the mixture is stirred for 5 minutes. The precipitate in suspension is then filtered through a No. 3 sintered glass filtration funnel. The cake obtained is then washed with 50 ml of methanol. The wet solid is drained and then dried under reduced pressure (6 kPa) at a temperature of about 40° C. After drying for 48 hours, 1.9 g of crude depolymerized heparin (sodium salt) are obtained. The yield obtained is 67%.

Purification:

1.9 g of crude depolymerized heparin obtained above and 19 ml of distilled water are placed in a 50 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.1 ml of aqueous 30% hydrogen peroxide solution is added. After stirring for about 2 hours at a temperature of about 20° C., the mixture is neutralized by adding 1N HCl, followed by addition of 2 g of sodium chloride. The solution is then filtered through a 0.45 μm membrane, and 14 ml of methanol are then poured in, and the mixture is then stirred for 15 minutes. 36 ml of methanol are then added, followed by stirring for 1 hour. Stirring is then stopped and the suspension is left to sediment for 15 minutes. The supernatant is then separated out and discarded (40 ml). 40 ml of methanol are added to the sedimented precipitate and the mixture is stirred for 5 minutes. The precipitate is left to resediment for about 20 minutes. The supernatant is separated out and discarded (50 ml). 50 ml of methanol are added to the sedimented precipitate, and the mixture is stirred for 5 minutes. The precipitate is left to resediment for about 20 minutes. The suspension is then filtered through a No. 3 sintered glass filtration funnel. The white cake obtained is then washed with 50 ml of methanol. The wet solid is drained and then dried under reduced pressure (6 kPa) at a temperature of about 40° C. After drying for 72 hours, 1.56 g of pure depolymerized heparin (sodium salt) are obtained. The yield obtained is 82%.

The characteristics of the depolymerized heparin thus obtained are as follows:
mean molecular weight: 2350 daltons
anti-Xa activity: 122 IU/mg
anti-IIa activity: 1.3 IU/mg
anti-Xa activity/anti-IIa activity ratio: 94

Example 5

Depolymerization and Conversion to the Sodium Salt (0.57% Water)

140 ml of dichloromethane are placed in an Erlenmeyer flask A. 20 g (0.019 mol) of benzyl ester of heparin (degree of esterification: 75%, benzethonium salt) obtained as described in example A, are added slowly, with stirring. The water content of the reaction medium is adjusted to 0.57%. After total dissolution, 3.5 ml (0.012 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in another Erlenmeyer flask B. After total dissolution, 10 g of Hyflo supercel Celite are added to the solution. The reaction mixture in the Erlenmeyer flask A is poured over 1 minute 30 seconds into the methanolic sodium acetate solution at a temperature of about 4° C., with magnetic stirring. After stirring for 5 minutes, the suspension is left to settle for 30 minutes. The clear part of the supernatant is separated out and discarded (400 ml). 400 ml of methanol are added to the sedimented precipitate, and the mixture is stirred for 5 minutes. The precipitate is left to resediment for about 1 hour. The supernatant is separated out and discarded (420 ml). 420 ml of methanol are added to the sedimented precipitate, and the mixture is stirred for 5 minutes. The suspension is then filtered through a No. 3 sintered glass filtration funnel. The cake obtained is then washed with 200 ml of methanol. The pale yellow wet solid is drained and then dried under reduced pressure (6 kPa) at a temperature of about 50° C. After drying for 18 hours, 6.66 g of crude depolymerized heparin are obtained, as the sodium salt in Celite (10 g). The yield obtained is 85%.

Saponification:

6.66 g (0.0101 mol) of the sodium salt of crude depolymerized heparin in Celite (10 g) obtained above and 47 ml of water are placed in a 50 ml Erlenmeyer flask. The suspension is filtered through a No. 3 sintered glass filtration funnel and rinsed twice with 15 ml of water. The filtrate obtained is placed in a 150 ml Erlenmeyer flask. 1.1 ml (0.011 mol) of 30% caustic soda are added with magnetic stirring, at a temperature of about 5° C. After addition, the mixture is stirred for 2 hours. The solution is neutralized by adding 1N HCl; then 9.5 g of sodium chloride are added. 66 ml of methanol are added to the reaction medium. After stirring for 15 minutes, 171 ml of methanol are added, followed by stirring for 1 hour. Stirring is then stopped and the suspension is left to sediment for ¾ hour at a temperature of about 5° C. The supernatant is then separated out and discarded (160 ml). 160 ml of methanol are added to the sedimented precipitate, and the mixture is stirred for 5 minutes. The precipitate is left to resediment for about 20 minutes. The supernatant is separated out and discarded (180 ml). 180 ml of methanol are added to the sedimented precipitate and the mixture is stirred for 5 minutes. The suspension is then filtered through a No. 3 sintered glass filtration funnel. The cake obtained is then washed twice with 50 ml of methanol. The wet solid is drained and then dried under reduced pressure (6 kPa) at a temperature of about 40° C. After drying for 18 hours, 4.53 g of crude depolymerized heparin (sodium salt) are obtained. The yield obtained is 74%.

Purification:

4.53 g of crude depolymerized heparin obtained above and 45 ml of distilled water are placed in a 100 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.25 ml of aqueous 30% hydrogen peroxide solution is added. After stirring for about 2 hours at a temperature of about 20° C., the mixture is neutralized by adding 1N HCl, followed by addition of 5.5 g of sodium chloride. The solution is then filtered through a 0.45 μm membrane, and 38 ml of methanol are then poured in, at a temperature of about 10° C. The solution is then brought to 20° C. and stirred for 15 minutes. 100 ml of methanol are then added, followed by stirring for 1 hour. Stirring is then stopped and the suspension is left to sediment for 20 minutes. The supernatant is then separated out and discarded (90 ml). 90 ml of methanol are added to the sedimented precipitate and the mixture is stirred for 5 minutes. The precipitate is left to resediment for about 25 minutes. The supernatant is separated out and discarded (100 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 50° C. After drying for 18 hours, 3.7 g of pure depolymerized heparin (sodium salt) are obtained. The yield obtained is 82%.

The characteristics of the depolymerized heparin thus obtained are as follows:

mean molecular weight: 2200 daltons
anti-Xa activity: 120 IU/mg
anti-IIa activity: 1.4 IU/mg
anti-Xa activity/anti-IIa activity ratio: 86

Example 6

Depolymerization and Conversion to the Sodium Salt (1.8% Water)

140 ml of dichloromethane are placed in an Erlenmeyer flask A. 20 g (0.019 mol) of benzyl ester of heparin (degree of esterification: 75%, benzethonium salt) obtained as described in example A, are added slowly, with stirring. The water content of the reaction medium is adjusted to 1.8%. After total dissolution, 3.5 ml (0.012 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in another Erlenmeyer flask B. After total dissolution, 10 g of Hyflo supercel Celite are added to the solution. The reaction mixture in the Erlenmeyer flask A is poured over 1 minute 30 seconds into the methanolic sodium acetate solution at a temperature of about 4° C., with magnetic stirring. After stirring for 5 minutes, the suspension is left to settle for 30 minutes. The clear part of the supernatant is separated out and discarded (400 ml). 400 ml of methanol are added to the sedimented precipitate, and the mixture is stirred for 5 minutes. The precipitate is left to resediment for about 1 hour. The supernatant is separated out and discarded (420 ml). 420 ml of methanol are added to the sedimented precipitate and the mixture is stirred for 5 minutes. The precipitate in suspension is then filtered through a No. 3 sintered glass filtration funnel. The cake obtained is then washed with 200 ml of methanol. The pale yellow wet solid is drained and then dried under reduced pressure (6 kPa) at a temperature of about 50° C. After drying for 18 hours, 7.54 g of crude depolymerized heparin are obtained, as the sodium salt in Celite (10 g). The yield obtained is 96%.

Saponification:

7.54 g (0.0101 mol) of the sodium salt of crude depolymerized heparin in Celite (10 g) obtained above and 53 ml of water are placed in a 50 ml Erlenmeyer flask. The solution is filtered through a No. 3 sintered glass filtration funnel and rinsed twice with 15 ml of water. The filtrate obtained is placed in a 150 ml Erlenmeyer flask. 1.25 ml (0.012 mol) of 30% caustic soda are added with magnetic stirring, at a temperature of about 4° C. After addition, the mixture is stirred for 2 hours. The solution is neutralized by adding 1N HCl; then 10.5 g of sodium chloride are added. 70 ml of methanol are added to the reaction medium. After stirring for 15 minutes, 190 ml of methanol are added, followed by stirring for 1 hour. Stirring is then stopped, and the suspension is left to sediment for % hour at a temperature of about 4° C. The supernatant is then separated out and discarded (180 ml). 180 ml of methanol are added to the sedimented precipitate, and the mixture is stirred for 5 minutes. The precipitate is left to resediment for about 20 minutes. The supernatant is separated out and discarded (180 ml). 180 ml of methanol are added to the sedimented precipitate, and the mixture is stirred for 5 minutes. The precipitate in suspension is then filtered through a No. 3 sintered glass filtration funnel. The cake obtained is then washed twice with 50 ml of methanol. The wet solid is drained and then dried under reduced pressure (6 kPa) at a temperature of about 50° C. After drying for 18 hours, 5.53 g of crude depolymerized heparin (sodium salt) are obtained. The yield obtained is 80%.

Purification:

5.53 g of crude depolymerized heparin obtained above and 55 ml of distilled water are placed in a 100 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.31 ml of aqueous 30% hydrogen peroxide solution is added. After stirring for about 2 hours at a temperature of about 20° C., the mixture is neutralized by adding 1N HCl, followed by addition of 7 g of sodium chloride. The solution is then filtered through a 0.45 μm membrane, and 49 ml of methanol are then poured in, at a temperature of about 10° C. The solution is then brought to 20° C. and stirred for 15 minutes. 126 ml of methanol are then added, followed by stirring for 1 hour. Stirring is then stopped and the suspension is left to sediment for 20 minutes. The supernatant is then separated out and discarded (105 ml). 105 ml of methanol are added to the sedimented precipitate, and the mixture is stirred for 5 minutes. The precipitate is left to resediment for about 25 minutes. The supernatant is separated out and discarded (110 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 55° C. After drying for 18 hours, 4.53 g of pure depolymerized heparin (sodium salt) are obtained. The yield obtained is 82%.

The characteristics of the depolymerized heparin thus obtained are as follows:
mean molecular weight: 2600 daltons
anti-Xa activity: 105 IU/mg
anti-IIa activity: 3.1 IU/mg
anti-Xa activity/anti-IIa activity ratio: 34.

Example 7

Depolymerization and Conversion to the Sodium Salt (2.5% Water)

140 ml of dichloromethane are placed in an Erlenmeyer flask A. 20 g (0.019 mol) of benzyl ester of heparin (degree of esterification: 75%, benzethonium salt) obtained as described in example A, are added slowly, with stirring. The water content of the reaction medium is adjusted to 2.5%. After total dissolution, 3.5 ml (0.012 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in an Erlenmeyer flask B. After total dissolution, 10 g of Hyflo supercel Celite are added to the solution. The reaction mixture in the Erlenmeyer flask A is poured over 1 minute 30 seconds into the methanolic sodium acetate solution at a temperature of about 4° C., with magnetic stirring. After stirring for 5 minutes, the suspension is left to settle for 1 hour. The clear part of the supernatant is separated out and discarded (400 ml). 400 ml of methanol are added to the sedimented precipitate, and the mixture is stirred for 5 minutes. The precipitate is left to resediment for about 30 minutes. The clear part of the supernatant is separated out and discarded (400 ml). The precipitate in suspension is then filtered through a No. 3 sintered glass filtration funnel. The cake obtained is then washed with 200 ml of methanol. The pale yellow wet solid is drained and then dried under reduced pressure (6 kPa) at a temperature in the region of 50° C. After drying for 18 hours, 7.78 g of crude depolymerized heparin are obtained, as the sodium salt in Celite (10 g). The yield obtained is 99.6%.
Saponification:

7.78 g (0.0119 mol) of the sodium salt of crude depolymerized heparin in Celite (10 g) obtained above and 79 ml of water are placed in a 50 ml Erlenmeyer flask. The suspension is filtered through a No. 3 sintered glass filtration funnel and rinsed twice with 15 ml of water. The filtrate obtained is placed in a 150 ml Erlenmeyer flask. 1.3 ml (0.012 mol) of 30% caustic soda are added with magnetic stirring, at a temperature of about 4° C. After addition, the mixture is stirred for 2 hours. The solution is neutralized by adding 1N HCl; then 10 g of sodium chloride are added. 60 ml of methanol are added to the reaction medium. After stirring for 15 minutes, 190 ml of methanol are added, followed by stirring for 1 hour. Stirring is then stopped and the suspension is left to sediment for ¾ hour at a temperature of about 4° C. The supernatant is then separated out and discarded (180 ml). 180 ml of methanol are added to the sedimented precipitate and the mixture is stirred for 5 minutes. The precipitate is left to resediment for about 20 minutes. The supernatant is separated out and discarded (180 ml). 180 ml of methanol are added to the sedimented precipitate and the mixture is stirred for 5 minutes. The precipitate in suspension is then filtered through a No. 3 sintered glass filtration funnel. The cake obtained is then washed twice with 50 ml of methanol. The wet solid is drained and then dried under reduced pressure (6 kPa) at a temperature of about 50° C. After drying for 18 hours, 5.87 g of crude depolymerized heparin (sodium salt) are obtained. The yield obtained is 82%.
Purification:

5.87 g of crude depolymerized heparin obtained above and 59 ml of distilled water are placed in a 100 ml Erlenmeyer flask. The mixture is brought to 40° C. with magnetic stirring. The pH is brought to 9.7±0.1 by addition of 1N sodium hydroxide. The reaction medium is filtered through a 0.45 µm membrane, and 0.34 ml of aqueous 30% hydrogen peroxide solution is added. After stirring for about 2 hours at a temperature of about 20° C., the mixture is neutralized by adding 1N HCl, followed by addition of 7 g of sodium chloride. The solution is then filtered through a 0.45 µm membrane, and 49 ml of methanol are then poured in, at a temperature of about 10° C. The solution is then brought to 20° C. and stirred for 15 minutes. 126 ml of methanol are then added, followed by stirring for 1 hour. Stirring is then stopped and the suspension is left to sediment for 20 minutes. The supernatant is then separated out and discarded (105 ml). 105 ml of methanol are added to the sedimented precipitate, and the mixture is stirred for 5 minutes. The precipitate is left to resediment for about 25 minutes. The supernatant is separated out and discarded (110 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 55° C. After drying for 18 hours, 5.21 g of pure depolymerized heparin (sodium salt) are obtained. The yield obtained is 89%.

The characteristics of the depolymerized heparin thus obtained are as follows:
mean molecular weight: 3550 daltons
anti-Xa activity: 99 IU/mg
anti-IIa activity: 13.4 IU/mg
anti-Xa activity/anti-IIa activity ratio: 7.4.

Example 8

Depolymerization and Conversion to the Sodium Salt (0.5 Equivalent of Base)

140 ml of dichloromethane are placed in an Erlenmeyer flask A. 20 g (0.019 mol) of benzyl ester of heparin (degree of esterification: 75%, benzethonium salt) obtained as described in example A, are added slowly, with stirring. After total dissolution at a temperature of about 30° C. and cooling to a temperature of about 20° C., 1.75 ml (0.006 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in an Erlenmeyer flask B. The reaction mixture in the Erlenmeyer flask A is poured into the methanolic sodium acetate solution at a temperature of about 4° C., with magnetic stirring. After stirring for 1 hour, the suspension is left to settle for 2 hours. The clear part of the supernatant is separated out and discarded (420 ml). 420 ml of methanol are added to the sedimented precipitate, and the mixture is stirred for 30 minutes. The precipitate is left to resediment for about 18 hours. The clear part of the supernatant is separated out and discarded (400 ml). 400 ml of methanol are added to the sedimented precipitate and the mixture is stirred for 30 minutes. The supernatant is separated out and discarded (400 ml). The precipitate in suspension is then filtered through a No. 3 sintered glass filtration funnel. The cake obtained is then washed with twice 100 ml of methanol. The pale yellow wet solid is drained and then dried under reduced pressure (6 kPa) at a temperature of about 60° C. After drying, 5.7 g of crude depolymerized heparin are obtained, as the sodium salt. The yield obtained is 73%.

Saponification:

5.7 g (0.0086 mol) of the sodium salt of crude depolymerized heparin obtained above and 53 ml of water are placed in a 100 ml Erlenmeyer flask. 0.93 ml (0.009 mol) of 30% caustic soda is added with magnetic stirring, at a temperature of about 4° C. After addition, the mixture is stirred for 2 hours. The solution is neutralized by adding 1N HCl; then 6 g of sodium chloride are added. 42 ml of methanol are added to the reaction medium. After stirring for 15 minutes, 108 ml of methanol are added, followed by stirring for 30 minutes. Stirring is then stopped and the suspension is left to sediment for 30 minutes at a temperature of about 4° C. The supernatant is then separated out and discarded (180 ml). 180 ml of methanol are added to the sedimented precipitate, and the mixture is stirred for 5 minutes. The precipitate is left to resediment for about 30 minutes. The supernatant is separated out and discarded (170 ml). 170 ml of methanol are added to the sedimented precipitate and the mixture is stirred for 30 minutes. The precipitate in suspension is then filtered through a No. 3 sintered glass filtration funnel. The cake obtained is then washed with twice 30 ml of methanol. The wet solid is drained and then dried under reduced pressure at a temperature of about 60° C. After drying, 3.5 g of crude depolymerized heparin (sodium salt) are obtained. The yield obtained is 67.4%.

Purification:

3.5 g of crude depolymerized heparin obtained above and 35 ml of distilled water are placed in a 100 ml Erlenmeyer flask. The mixture is brought to 40° C. with magnetic stirring. The pH is brought to 9.6±0.1 by addition of 1N sodium hydroxide. The reaction medium is filtered through a 0.45 μm membrane, and 0.18 ml of aqueous 30% hydrogen peroxide solution is added. After stirring for about 2 hours at a temperature of about 20° C., the mixture is neutralized by adding 1N HCl, followed by addition of 3.6 g of sodium chloride. The solution is then filtered through a 0.45 μm membrane, and 27 ml of methanol are then poured in, at a temperature of about 10° C. The solution is then brought to 20° C. and stirred for 15 minutes. 65 ml of methanol are then added, followed by stirring for 30 minutes. Stirring is then stopped and the suspension is left to sediment for 30 minutes. The supernatant is then separated out and discarded (80 ml). 80 ml of methanol are added to the sedimented precipitate, and the mixture is stirred for 30 minutes. The precipitate is left to resediment for about 30 minutes. The supernatant is separated out and discarded (70 ml). 70 ml of methanol are added to the sedimented precipitate and the mixture is stirred for 30 minutes. The precipitate in suspension is then filtered through a No. 3 sintered glass filtration funnel. The white cake obtained is then washed twice with 30 ml of methanol. The wet solid is drained and then dried under reduced pressure at a temperature of about 60° C. After drying, 2.8 g of pure depolymerized heparin (sodium salt) are obtained. The yield obtained is 80%. The characteristics of the depolymerized heparin thus obtained are as follows:

mean molecular weight: 2900 daltons
anti-Xa activity: 146.1 IU/mg
anti-IIa activity: 5.1 IU/mg
anti-Xa activity/anti-IIa activity ratio: 28.6.

Example 9

Depolymerization and Conversion to the Sodium Salt (0.6 Equivalent of Base)

280 ml of dichloromethane are placed in a three-necked flask A. 40 g (0.024 mol) of benzyl ester of heparin (degree of esterification: 75%, benzethonium salt) obtained as described in example A, are added slowly, with stirring. After total dissolution at a temperature of about 30° C. and cooling to a temperature of about 20° C., 4.2 ml (0.014 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in an Erlenmeyer flask B. Half of the reaction mixture in the three-necked flask A is poured into the methanolic sodium acetate solution at a temperature of about 4° C., with magnetic stirring. After stirring for 1 hour, the suspension is left to settle. The clear part of the supernatant is separated out and discarded (310 ml). 310 ml of methanol are added to the sedimented precipitate, and the mixture is stirred for 1 hour. The precipitate is left to resediment for about 18 hours. The clear part of the supernatant is separated out and discarded (400 ml). 400 ml of methanol are added to the sedimented precipitate and the mixture is stirred for 1 hour. The supernatant is separated out and discarded (300 ml). The precipitate in suspension is then filtered through a No. 3 sintered glass filtration funnel. The cake obtained is then washed with twice 100 ml of methanol. The pale yellow wet solid is drained and then dried under reduced pressure at a temperature of about 60° C. After drying, 6 g of crude depolymerized heparin are obtained, as the sodium salt. The yield obtained is 77%.

Saponification:

6 g (0.0091 mol) of the sodium salt of crude depolymerized heparin obtained above and 56 ml of water are placed in a 250 ml Erlenmeyer flask. 1 ml (0.010 mol) of 30% caustic soda is added with magnetic stirring, at a temperature of about 4° C. After addition, the mixture is stirred for 2 hours. The solution is neutralized by adding 1N HCl; then 6.4 g of sodium chloride are added. 45 ml of methanol are added to the reaction medium. After stirring for 15 minutes, 115 ml of methanol are added, followed by stirring for 30 minutes. Stirring is then stopped and the suspension is left to sediment for 30 minutes at a temperature of about 4° C. The supernatant is then separated out and discarded (170 ml). 170 ml of methanol are added to the sedimented precipitate and the mixture is stirred for 30 minutes. The precipitate is left to resediment for about 30 minutes. The supernatant is separated out and discarded (140 ml). 140 ml of methanol are added to the sedimented precipitate, and the mixture is stirred for 30 minutes. The precipitate in suspension is then filtered through a No. 3 sintered glass filtration funnel. The cake obtained is then washed twice with 30 ml of methanol. The wet solid is drained and then dried under reduced pressure at a temperature of about 60° C. After drying, 3.6 g of crude depolymerized heparin (sodium salt) are obtained. The yield obtained is 65.3%.

Purification:

3.5 g of crude depolymerized heparin obtained above and 35 ml of distilled water are placed in a 100 ml Erlenmeyer flask. The mixture is brought to 40° C. with magnetic stirring. The pH is brought to 9.6±0.1 by addition of 1N sodium hydroxide. The reaction medium is filtered through a 0.45 μm membrane, and 0.18 ml of aqueous 30% hydrogen peroxide solution is added. After stirring for about 2 hours at a temperature of about 20° C., the mixture is neutralized by adding 1N HCl, followed by addition of 3.5 g of sodium chloride. The solution is then filtered through a 0.45 μm membrane and 25 ml of methanol are then poured in, at a temperature of about 10° C. The solution is then brought to 20° C. and stirred for 15 minutes. 63 ml of methanol are then added, followed by stirring for 30 minutes. Stirring is then stopped and the suspension is left to sediment for 30 minutes. The supernatant is then separated out and discarded (70 ml). 70 ml of methanol are added to the sedimented precipitate, and the mixture is stirred for 30 minutes. The precipitate is left to resediment for a few minutes. The suspension is then filtered through a No. 3 sintered glass filtration funnel. The white cake obtained is then washed twice with 30 ml of methanol. The wet solid is drained and then dried under reduced pressure at a temperature of about 60° C. After drying, 2.5 g of pure depolymerized heparin (sodium salt) are obtained. The yield obtained is 71.4%.

The characteristics of the depolymerized heparin thus obtained are as follows:
mean molecular weight: 2600 daltons
anti-Xa activity: 150.5 IU/mg
anti-IIa activity: 3.2 IU/mg
anti-Xa activity/anti-IIa activity ratio: 47.

Example 10

Depolymerization and Conversion to the Sodium Salt (0.8 Equivalent of Base)

70 ml of dichloromethane are placed in an Erlenmeyer flask A. 10 g (0.006 mol) of benzyl ester of heparin (degree of esterification: 75%, benzethonium salt), obtained as described in example A, are added slowly, with stirring. After total dissolution at a temperature of about 30° C. and cooling to a temperature of about 20° C., 1.38 ml (0.004 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 30 g of anhydrous sodium acetate in 300 ml of methanol is prepared in an Erlenmeyer flask B. The reaction mixture in the Erlenmeyer flask A is poured over 1 minute 15 seconds into the methanolic sodium acetate solution at a temperature of about 4° C., with magnetic stirring. After stirring for 5 minutes, the suspension is left to settle for 1 hour. The clear part of the supernatant is separated out and discarded (190 ml). 190 ml of methanol are added to the sedimented precipitate, and the mixture is stirred for minutes. The precipitate is left to resediment for about 30 minutes. The clear part of the supernatant is separated out and discarded (190 ml). 190 ml of methanol are added to the sedimented precipitate, and the mixture is stirred for 30 minutes. The supernatant is separated out and discarded (190 ml). The precipitate in suspension is then filtered through a No. 3 sintered glass filtration funnel. The cake obtained is then washed with 150 ml of methanol. The pale yellow wet solid is drained and then dried under reduced pressure (6 kPa) at a temperature of about 40° C. After drying for 18 hours, 3.05 g of crude depolymerized heparin are obtained, as the sodium salt. The yield obtained is 80%.

Saponification:

3.05 g (0.0048 mol) of the sodium salt of crude depolymerized heparin obtained above and 21 ml of water are placed in a 100 ml Erlenmeyer flask. The solution is filtered through a No. 3 sintered glass filtration funnel and rinsed twice with 6 ml of water. The filtrate obtained is placed in a 150 ml Erlenmeyer flask. 0.6 ml (0.006 mol) of 30% caustic soda is added with magnetic stirring, at a temperature of about 4° C. After addition, the mixture is stirred for 2 hours. The solution is neutralized by adding 1N HCl; then 4 g of sodium chloride are added. 28 ml of methanol are added to the reaction medium. After stirring for 15 minutes, 72 ml of methanol are added, followed by stirring for 1 hour. Stirring is then stopped and the suspension is left to sediment for 30 minutes at a temperature of about 4° C. The supernatant is then separated out and discarded (80 ml). 80 ml of methanol are added to the sedimented precipitate and the mixture is stirred for 5 minutes. The precipitate is left to resediment for about 30 minutes. The supernatant is separated out and discarded (80 ml). 80 ml of methanol are added to the sedimented precipitate and the mixture is stirred for 30 minutes. The precipitate in suspension is then filtered through a No. 3 sintered glass. The cake obtained is then washed with 50 ml of methanol. The wet solid is drained and then dried under reduced pressure (6 kPa) at a temperature of about 40° C. After drying, 1.6 g of crude depolymerized heparin (sodium salt) are obtained. The yield obtained is 57%.

Purification:

1.6 g of crude depolymerized heparin obtained above and 16 ml of distilled water are placed in a 50 ml Erlenmeyer flask. The mixture is brought to 40° C. with magnetic stirring. The pH is brought to 9.6±0.1 by addition of 1N sodium hydroxide. The reaction medium is filtered through a 0.45 μm membrane, and 0.08 ml of aqueous 30% hydrogen peroxide solution is added. After stirring for about 2 hours at a temperature of about 20° C., the mixture is neutralized by adding 1N HCl, followed by addition of 2 g of sodium chloride. The solution is then filtered through a 0.45 μm membrane, and 14 ml of methanol are then poured in, at a temperature of about 10° C. The solution is then brought to 20° C. and stirred for 15 minutes. 36 ml of methanol are then added, followed by stirring for 1 hour. Stirring is then stopped and the suspension is left to sediment for 30 minutes. The supernatant is then separated out and discarded (50 ml). 50 ml of methanol are added to the sedimented precipitate and the mixture is stirred for 5 minutes. The precipitate is left to resediment for about 30 minutes. The supernatant is separated out and discarded (50 ml). The precipitate in suspension is then filtered through a No. 3 sintered glass filtration funnel. The wet solid is drained and then dried under reduced pressure (6 kPa) at a temperature of about 40° C. After drying, 1.25 g of pure depolymerized heparin (sodium salt) are obtained. The yield obtained is 78%.

The characteristics of the depolymerized heparin thus obtained are as follows:
mean molecular weight: 2400 daltons
anti-Xa activity: 154.3 IU/mg
anti-IIa activity: 1.6 IU/mg
anti-Xa activity/anti-IIa activity ratio: 96.4.

Example 11

Depolymerization and Conversion to the Sodium Salt 140 ml of dichloromethane are placed in an Erlenmeyer flask A. 20 g (0.019 mol) of benzyl ester of heparin (degree of esterification: 75%, benzethonium salt) obtained as described in example A, are added slowly, with stirring. After total dissolution at a temperature of about 40° C. and cooling to a temperature of about 20° C., 3.5 ml (0.011 mol) of tert-butyliminotri(pyrrolidino)phosphorane are added. The mixture is stirred at a temperature of about 20° C. for 24 hours. During this time, a solution of 60 g of anhydrous sodium acetate in 600 ml of methanol is prepared in an Erlenmeyer flask B. After total dissolution, 10 g of Hyflo supercel Celite are added to the solution. The reaction mixture in the Erlenmeyer flask A is poured over 1 minute 30 seconds into the methanolic sodium acetate solution at a temperature of about 4° C., with magnetic stirring. After stirring for 5 minutes, the suspension is left to settle for 30 minutes. The clear part of the supernatant is separated out and discarded (400 ml). 400 ml of methanol are added to the sedimented precipitate, and the mixture is stirred for 5 minutes. The precipitate is left to resediment for about 1 hour 20 minutes. The supernatant is separated out and discarded (250 ml). 250 ml of methanol are added to the sedimented precipitate and the mixture is stirred for 5 minutes. The precipitate in suspension is then filtered through a No. 3 sintered glass filtration funnel. The cake obtained is then washed with 200 ml of methanol. The pale yellow wet solid is drained and then dried under reduced pressure (6 kPa) at a temperature of about 40° C. After drying, 5.39 g of depolymerized heparin (benzyl ester, sodium salt) are obtained. The yield obtained is 69%.

Saponification:

5 g (0.0076 mol) of the depolymerized heparin (benzyl ester, sodium salt) obtained above and 35 ml of water are placed in a 50 ml Erlenmeyer flask. The solution is filtered through a No. 3 sintered glass filtration funnel and rinsed twice with 10 ml of water. The filtrate obtained is placed in a 250 ml Erlenmeyer flask. 1 ml (0.01 mol) of 30% caustic soda is added with magnetic stirring, at a temperature of about 4° C. After addition, the mixture is stirred for 2 hours. The solution is neutralized by adding 1N HCl; then 6 g of sodium chloride are added. 42 ml of methanol are added to the reaction medium. After stirring for 15 minutes, 104 ml of methanol are added, followed by stirring for 15 minutes. Stirring is then stopped and the suspension is left to sediment for 1 hour at a temperature of about 4° C. The supernatant is then separated out and discarded (140 ml). 140 ml of methanol are added to the sedimented precipitate and the mixture is stirred for 5 minutes. The precipitate is left to resediment for about 45 minutes. The supernatant is separated out and discarded (160 ml). 160 ml of methanol are added to the sedimented precipitate and the mixture is stirred for 5 minutes. The precipitate in suspension is then filtered through a No. 3 sintered glass filtration funnel. The cake obtained is then washed with 100 ml of methanol. The wet solid is drained and then dried under reduced pressure (6 kPa) at a temperature of about 40° C. After drying for 48 hours, 2.7 g of crude depolymerized heparin (sodium salt) are obtained. The yield obtained is 59%.

Purification:

2.6 g of crude depolymerized heparin obtained above and 25 ml of distilled water are placed in a 50 ml Erlenmeyer flask. The mixture is brought to 40° C. with magnetic stirring. The pH is brought to 9.7±0.1 by addition of 1N sodium hydroxide. The reaction medium is filtered through a 0.45 μm membrane, and 0.15 ml of aqueous 30% hydrogen peroxide solution is added. After stirring for about 2 hours at a temperature of about 20° C., the mixture is neutralized by adding 1N HCl, followed by addition of 3 g of sodium chloride. The solution is then filtered through a 0.45 μm membrane, and 21 ml of methanol are then poured in, at a temperature of about 10° C. The solution is then brought to 20° C. and stirred for 15 minutes. 54 ml of methanol are then added, followed by stirring for 1 hour. Stirring is then stopped and the suspension is left to sediment for 20 minutes. The supernatant is then separated out and discarded (50 ml). 50 ml of methanol are added to the sedimented precipitate and the mixture is stirred for 5 minutes. The precipitate is left to resediment for about 20 minutes. The supernatant is separated out and discarded (50 ml). The precipitate in suspension is then filtered through a No. 3 sintered glass filtration funnel. The white cake obtained is then washed with 50 ml of methanol. The wet solid is drained and then dried under reduced pressure (6 kPa) at a temperature of about 40° C. After drying for 18 hours, 2.35 g of pure depolymerized heparin (sodium salt) are obtained. The yield obtained is 90%.

The characteristics of the depolymerized heparin thus obtained are as follows:
mean molecular weight: 2400 daltons
anti-Xa activity: 167.5 IU/mg
anti-IIa activity: 1.1 IU/mg
anti-Xa activity/anti-IIa activity ratio: 152.

Example 12

Depolymerization and Conversion to the Sodium Salt (0.05% Water)

140 ml of dichloromethane are placed in an Erlenmeyer flask. 20 g (0.019 mol) of benzyl ester of heparin (degree of esterification: 75%, benzethonium salt), obtained as described in example A, are added slowly, with stirring. 20 g of 4 A molecular sieve are added to the reaction medium, and the water content is brought to 0.05%, while stirring slowly for 48 h. The supernatant is transferred under an inert atmosphere to an Erlenmeyer flask A. After total dissolution, 3.5 ml (0.012 mol) of 2-tert-butylimino-2-diethylamino-1,3-dimethylperhydro-1,2,3-diazaphosphorine are added. The mixture is stirred at a temperature of about 20° C. for 24 hours. During this time, a solution of 60 g of anhydrous sodium acetate in 600 ml of methanol is prepared in an Erlenmeyer flask B. After total dissolution, 10 g of Hyflo supercel Celite are added to the solution. The reaction mixture in the Erlenmeyer flask A is poured over about 2 minutes into the methanolic sodium acetate solution at a temperature of about 4° C., with magnetic stirring. After stirring for 15 minutes, the suspension is left to settle for 1 hour. The clear part of the supernatant is separated out and discarded (420 ml). 420 ml of methanol are added to the sedimented precipitate and the mixture is stirred for 15 minutes. The precipitate is left to resediment for about 1 hour. The supernatant is separated out and discarded (450 ml). 450 ml of methanol are added to the sedimented precipitate and the mixture is stirred for 15 minutes. The suspension is then filtered through a No. 3 sintered glass filtration funnel. The cake obtained is then washed with 200 ml of methanol. The pale yellow wet solid is drained and then dried under reduced pressure (6 kPa) at a temperature of about 50° C. After drying for 16 hours, 5.36 g of crude depolymerized heparin are obtained, as the sodium salt in Celite (10 g). The yield obtained is 68.6%.

Saponification:

5.36 g (0.00817 mol) of the sodium salt of crude depolymerized heparin in Celite (10 g) obtained above and 50 ml of water are placed in a 50 ml Erlenmeyer flask. The suspension is filtered through a No. 3 sintered glass filtration funnel and rinsed 4 times with 15 ml of water. The filtrate obtained is placed in a 150 ml Erlenmeyer flask. 1.01 ml (0.0122 mol) of 35% caustic soda are added with magnetic stirring, at a temperature of about 4° C. After addition, the mixture is stirred for 3 hours. The solution is neutralized by adding 1N HCl; then 11 g of sodium chloride are added. 77 ml of methanol are added to the reaction medium. After stirring for 15 minutes, 200 ml of methanol are added, followed by stirring for 1 hour. Stirring is then stopped and the suspension is left to sediment for 1 hour at a temperature of about 4° C. The supernatant is then separated out and discarded (240 ml). 240 ml of methanol are added to the sedimented precipitate and the mixture is stirred for 10 minutes. The precipitate is left to resediment for about 30 minutes. The supernatant is separated out and discarded (225 ml). 225 ml of methanol are added to the sedimented precipitate and the mixture is stirred for 10 minutes. The suspension is then filtered through a No. 3 sintered glass filtration funnel. The cake obtained is then washed with twice 50 ml of methanol. The wet solid is drained and then dried under reduced pressure (6 kPa) at a temperature of about 40° C. After drying for 18 hours, 2.65 g of crude depolymerized heparin (sodium salt) are obtained. The yield obtained is 53.7%.

Purification:

2.65 g of crude depolymerized heparin obtained above and 26.5 ml of distilled water are placed in a 100 ml Erlenmeyer flask. The mixture is brought to 40° C. with magnetic stirring. The pH is brought to 9.7±0.1 by addition of 1N sodium hydroxide. The reaction medium is filtered through a 0.45 µm membrane, and 0.25 ml of aqueous 30% hydrogen peroxide solution is added. After stirring for about 2 hours at a temperature of about 20° C., the mixture is neutralized by adding 1N HCl, followed by addition of 3 g of sodium chloride. The solution is then filtered through a 0.45 µm membrane, and 21 ml of methanol are then poured in, at a temperature of about 10° C. The solution is then brought to 20° C. and stirred for 15 minutes. 54 ml of methanol are then added, followed by stirring for 1 hour. Stirring is then stopped and the suspension is left to sediment for 45 minutes. The supernatant is then separated out and discarded (46 ml). 46 ml of methanol are added to the sedimented precipitate and the mixture is stirred for 5 minutes. The precipitate is left to resediment for about 30 minutes. The supernatant is separated out and discarded (50 ml). 50 ml of methanol are added and the precipitate in suspension is then filtered through a No. 4 sintered glass filtration funnel. The white cake obtained is then washed with 2 portions of 10 ml of methanol. The wet solid is drained and then dried under reduced pressure (6 kPa) at a temperature of about 50° C. After drying for 18 hours, 2.363 g of pure depolymerized heparin (sodium salt) are obtained. The yield obtained is 89.1%.

The characteristics of the depolymerized heparin thus obtained are as follows:
mean molecular weight: 2500 Daltons
anti-Xa activity: 192 IU/mg
anti-IIa activity: 1.3 IU/mg
anti-Xa activity/anti-IIa activity ratio: 148.

We claim:
1. A mixture of sulfated oligosaccharides having the following characteristics:
a mean molecular weight of from about 1500 daltons to about 3000 daltons,
an anti-Xa activity of between 154.3 IU/mg and 192 IU/mg,
an anti-IIa activity of less than about 10 IU/mg, and
an anti-Xa activity/anti-IIa activity ratio of greater than about 30;
wherein the constituent oligosaccharides of the mixture contain 2 to 26 saccharide units,
wherein a portion of the constituent oligosaccharides of the mixture have a 4,5-unsaturated uronic acid 2-O-sulfate unit at one of their ends, and wherein the constituent oligosaccharides of the mixture contain a hexasaccharide fraction, wherein from about 8% to about 15% of the hexasaccharide fraction of the mixture is the hexasaccharide ΔIIa-IIs-Is of formula:

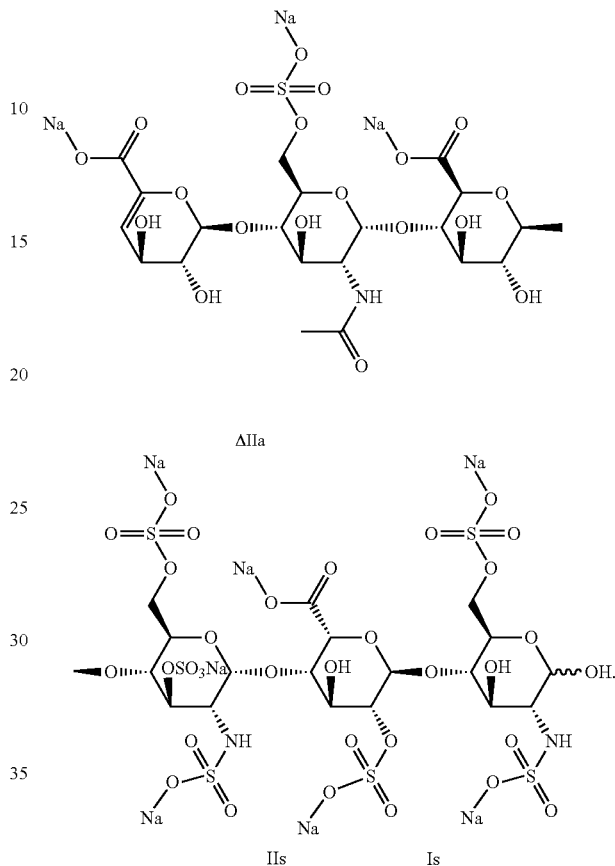

2. The mixture of claim 1, wherein the mixture exhibits an anti-IIa activity of less than 5 IU/mg.
3. The mixture of claim 1, wherein the mixture exhibits an anti-Xa activity/anti-IIa activity ratio of greater than about 50.
4. The mixture of claim 1, wherein the mixture has a mean molecular weight of between 2000 and 3000 Daltons.
5. The mixture of claim 1, wherein the mixture is prepared by a process comprising:
depolymerising a quaternary ammonium salt of a benzyl ester of heparin in a reaction medium comprising an organic solvent and an organic base with a pKa greater than 20, wherein the organic base is selected from phosphazenes, wherein the base:ester molar ratio is from 0.6 to 2, controlling the water content of the reaction medium to be 0.2% or less by measuring the water content and determining whether adjustment is necessary;
wherein the depolymerization and/or water control steps are performed under conditions such that a mixture of sulfated oligosaccharides having an anti-Xa activity of between 154.3 IU/mg and 192 IU/mg is produced.
6. The mixture of claim 5, wherein the organic base with a pKa greater than 20 is 2-tert-butylimino-2-diethylamino-1,3-dimethylperhydro-1,2,3-diazaphosphorine.
7. A pharmaceutical composition comprising the mixture of claim 1 and an inert excipient.

* * * * *